United States Patent [19]

Gale et al.

[11] 3,995,027

[45] Nov. 30, 1976

[54] ANTI-VIRAL METHOD IN ANIMALS

[75] Inventors: Charles Gale, Indianapolis; Larry R. McDougald, Greenfield, both of Ind.

[73] Assignee: Eli Lilly and Company, Indianapolis, Ind.

[22] Filed: June 4, 1975

[21] Appl. No.: 583,820

[52] U.S. Cl.................................. 424/115; 424/120; 424/122; 424/181
[51] Int. Cl.² ................... A61K 35/66; A61K 31/71
[58] Field of Search ............ 424/122, 181, 115, 120

[56] References Cited
OTHER PUBLICATIONS

Kitame et al., Journal of Antibiotics, vol. 27, (July–-Dec. 1974), pp. 884, 885 & 887.

*Primary Examiner*—Sam Rosen
*Attorney, Agent, or Firm*—Dwight E. Morrison; Everet F. Smith

[57] ABSTRACT

A method for moderating the effects of viral infections in animals by administration thereto of a polyether ionophorous antibiotic selected from the group consisting of monensin, A-28086, A28695, A28695A, A28695B, nigericin, and carbomonensin.

6 Claims, No Drawings

ANTI-VIRAL METHOD IN ANIMALS

BACKGROUND OF THE INVENTION

1. Field of the Invention

It is well-known that animals, e.g., cattle, dogs, and swine, as well as poultry, often suffer from infectious diseases caused by viruses. Such diseases result in serious economic losses to the owners of such animals and poultry. Effective methods of moderating the effects of or preventing these viral infections and diseases are continuously sought in order to reduce the economic losses.

2. Description of the Prior Art

In the prior art, U.S. application Ser. No. 569,740, filed Apr. 21, 1975, describes antibiotic A-28086 complex, a process for its preparation, and methods for the separation of the complex into antibiotic factors A-28086A, A-28086B, and A-28086D. The reference also teaches that the A-28086 compounds are anti-coccidial, antifungal, antibacterial, anti-PPLO, insecticidal and acaricidal, as well as anti-viral agents. In particular, A-28086 factor A, also referred to as A-28086A, is active against Type III poliovirus, vaccinia virus, herpes virus and Semliki Forest virus. In addition, antibiotic A-28086A is also taught as being active against Transmissible Gastroenteritis virus, Newcastle Disease virus, and Infectious Bovine Rhinotracheitis virus. All of these activities have been demonstrated by tissue-culture tests.

Follett et al., In "The Mode of Action of Rifamycins and Related Compounds on Poxvirus," appearing in *Advances in Virus Research*, Vol. 18, edited by Lauffer et al., teach that the antibiotic rifamycin S was an active antiviral against vaccinia virus, but the amount of drug required for complete inhibition was too high for clinical use. The effect of the drug was reported as being specific and not the result of a toxic effect of the drug on host cell metabolism. Rifamycin is not classified as a polyether inophorous antibiotic.

SUMMARY OF THE INVENTION

This invention is directed to a method of moderating the effects of viral infections in swine and dogs by the administration thereunto of a polyether inophorous antibiotic.

DESCRIPTION OF THE PREFERRED EMBODIMENTS

This invention relates to a method of moderating the effects of viral infections in dogs and swine. More particularly this invention relates to the method of moderating the effects of viral infections in these animals by the administration to the animals of an antibiotic. Of course, the ultimate moderation of the effects of these viral infections in the animals would be the prevention of the viral infections.

The antibiotics useful in this method are identified as polyether ionophorous antibiotics, most of which have been known for some time. A special property of these antibiotics is their ability to effect the transport of cations across membranes. Although not fully understood, their mode of action is presumed to be either that of simple carriers that confer lipid solubility on the ions transported, or a channel mechanism whereby stacks of molecules stretch across the membrane to form a hydrophilic tunnel. See "The Polyether Antibiotics" by Westley and Berger, *Handbook of Microbiology*, Vol. III: *Microbial Products*.

The polyether ionophorous antibiotics found useful in this novel method are produced by various streptomycetes, and are identified as follows:

The A204 complex, which includes antibiotics A204I, A204II, and A204III, and the methods for production are disclosed in U.S. Pat. No. 3,705,238 (Dec. 5, 1972). The antibiotics are co-produced by culturing *Streptomyces albus* strain NRRL 3384.

Deshydroxymethylmonensin, or dihydromonensin, is described by U.S. Pat. No. 3,832,358 (Aug. 27, 1974), together with methods for its production. Monensin is produced by culturing *Streptomyces cinnamonensis* ATCC 15413, the sodium salt prepared, and allowed to react with sodium borohydride in absolute ethanol, to yield deshydroxymethylmonensin, having a melting point of about 78°–80° C.

Antibiotics A28695A, and A28695B, and a process for their production are disclosed in U. S. Pat. No. 3,839,558 (Oct. 1, 1974). These antibiotics are produced by culturing *Streptomyces albus* strain NRRL 3883.

The antibiotic A3823 complex is described in U.S. Pat. No. 3,501,568 (Mar. 17, 1970). This A3823 complex comprises four factors and is produced by fermentation of *Streptomyces cinnamonensis* ATCC 15413. Monensin is one of the factors of this complex, as is monensis B.

The antibiotic Nigericin has been reported in the literature by Harned et al., "Nigericin, A New Crystalline Antibiotic from an Unidentified Streptomyces." *Antibiotics and Chemotherapy* 1:594–596 (1951). This antibiotic is produced by culturing a strain of *Streptomyces violaceoniger* NRRL B1356, as described in U. S. Pat. No. 3,555,150 (Jan. 12, 1971).

Dianemycin, (A150), is disclosed in U.S. Pat. No. 3,577,531 (May 4, 1971). Dianemycin is an acidic molecule produced by cultivating under controlled conditions a strain of *Streptomyces spp.* NRRL 3444.

Antibiotic X-537A, also known as Lasalocid, is described by Berger et al., J. Am. Chem. Soc. 73, 5295 (1951). This antibiotic is produced by culturing a strain of *Streptomyces spp.* NRRL 3382, as described in U.S. Pat. No. 3,719,753 (Mar. 6, 1973).

Antibiotic X-206 is also described by Berger et al., supra. Antibiotic X-206 is produced by culturing a strain of a Streptomyces organism available from the International Center of Information on Antibiotics, c/o L. Delcambe, 32, Bd. de la Constitution, Liege, Belgium, which lists the organism on page 31 of its Bulletin No. 3 (1966). The production of X-206 is described in U.S. Pat. No. 3,794,732 (Feb. 26, 1974).

Novel monoether derivatives of antibiotic A204I, and their method of preparation are described in U.S. application Ser. No. 524,178, filed Nov. 11, 1974 now U.S. Pat. No. 3,907,832. Antibiotic A204I is produced by culturing *Streptomyces albus* strain NRRL 3384, as described in U.S. Pat. No. 3,705,238 (Dec. 5, 1972).

The antibiotic A-28086 complex, a process for its preparation, and methods for the separation of the antibiotic complex into its antibiotic factors is described and disclosed in U.S. application Ser. No. 569,740, filed Apr. 21, 1975. This antibiotic complex is produced by fermentation of *Streptomyces aureofaciens* strains NRRL 5758 and NRRL 8892.

Carbomonensin, also identified as Metabolite A-27106, is disclosed and described in U.S. application Ser. No. 473,016, filed May 24, 1974 now U.S. Pat. No. 3,832,619. This antibiotic is produced by reaction of monensin and glucose with an enzyme system produced by submerged culture of *Streptomyces candidus* NRRL 5449.

The polyether ionophorous antibiotics useful in the novel method of this invention are thus made readily available according to previously published procedures, or their preparation is taught in succeeding portions of this specification.

The following examples are provided to more fully illustrate the preparation of the monoether derivatives of antibiotic A204I.

EXAMPLE 1

Preparation of A204I Methyl Ether Derivative from A204I Sodium Salt

Antibiotic A204I sodium salt (20 g) was dissolved in methanol (1 l.), and water (500 ml) was added slowly. This solution was adjusted to pH 3.0 by the addition of 6 N hydrochloric acid. The resulting solution was stirred for one hour and then was extracted with an equal volume of chloroform. This chloroform extract was evaporated to dryness under vacuum.

The resulting residue (2 g) was dissolved in 10 ml of a benzene-ethyl acetate (7:3) mixture, and this solution was chromatographed on a 2- × 51-cm silica gel column (Woelm), eluting with the same benzene-ethyl acetate solvent mixture. Elution was monitored by thin-layer chromatography. The fractions containing A204I methyl ether derivative were combined and evaporated to dryness under vacuum. A204I methyl ether derivative (1.4 g) crystallized from methanol-water, mp 115°–117° C, $[\alpha]_D^{25}$ + 75.00 (c=1, $CH_3OH$); $pK_a'$ (66 percent aqueous dimethylformamide) 7.1. This A204I methyl ether derivative was further identified by elemental analyses.

EXAMPLE 2

Preparation of A204I methyl ether derivative from A204I antibiotic A204I in the acid form (400 mg) was dissolved in methanol (10 ml), and water (5 ml) was added. After being allowed to stand one hour, the solution was evaporated under vacuum. The resulting residue was chromatographed as described in Example 1, to give A204I methyl ether derivative.

EXAMPLE 3

Preparation of A204I n-Propyl Ether Derivative

Antibiotic A204I in the acid form (10 g) was dissolved in n-propanol (200 ml). This solution was allowed to stand at room temperature for 1 week and then was evaporated to dryness in vacuo. The residue thus obtained was a mixture of starting A204I and the desired product.

This mixture was dissolved in 20 ml. of benezene-ethyl acetate (7:3), and this solution was applied to a 4- × 120-cm silica gel (Grade 62) column, eluting with benzene-ethyl acetate (7:3). Elution was monitored by thin-layer chromatography on silica gel in benzene-ethyl acetate (3:2), using $H_2SO_4$ spray for detection. The desired A204I n-propyl ether derivative was eluted from the column before the remaining starting material was eluted. The fractions containing A-204I n-propyl ether derivative were combined and evaporated to dryness. The residue crystallized from acetone-water to give 4.15 g of A-204I n-propyl ether derivative, mp 114°–116° C, $[\alpha]_D^{25}$ + 73.08 (c=1, $CH_3OH$); $pK_a'$ (66 percent aqueous dimethylformamide) 7.8. This A204I n-propyl ether derivative was further identified by elemental analyses.

EXAMPLE 4

Preparation of A204I Ethyl Ether Derivative

A204I ethyl ether derivative was prepared from antibiotic A204I and ethanol by the method used in Example 3, crystallized from acetonitrile, mp 117°–120° C., $[\alpha]_D^{25}$ + 74.23 (c=1, $CH_3OH$); $pK_a'$ (66 percent aqueous dimethylformamide) 8.0. This A204I ethyl ether derivative was further identified by elemental analyses.

The A2086 antibiotics useful in this novel invention are produced by *Streptomyces aureofaciens* cultures which are on unrestricted deposit with and a part of the stock culture collection of the U.S. Department of Agriculture, Agricultural Research Service, Northern Regional Research Laboratory, Peoria, Illinois, 61604, from which the cultures are available to the public under the numbers NRRL 5758, and NRRL 8092.

The A-28086 factors are structurally related to each other. At least four antibiotic factors are coproduced during the fermentation and are obtained as a mixture. The factors are separated from each other, and factors A, B, and D are isolated as individual compounds as hereinafter described. The mixture of A-28086 factors is soluble in most organic solvents, but is insoluble in water.

The following paragraphs describe the physical and spectral properties of A-28086 factors A and B.

Antibiotic A-28086 factor A crystallizes from actone-water. A-28086 factor A melts at about 98°–100° C., resolidifies and remelts at about 195°–200° C. Elemental analysis of factor A gave the following average percentage composition: carbon, 66.69 percent; hydrogen, 9.85 percent; oxygen, 23.10 percent. The empirical formula proposed for factor A is $C_{43}H_{72}O_{11}$.

Factor A has an apparent molecular weight of 764, as determined by mass spectrometry.

The infrared spectrum of factor A in chloroform shows the following observed absorption maxima: 2.85, 3.34, 5.83, 6.82, 7.22, 7.53 (weak), 7.78 (weak), 8.75 (strong), 8.95 (strong), 9.15, 9.50 (strong), 9.55 (strong), 9.60, 9.85, 10.15, 10.45, and 10.70 (weak) microns.

The ultraviolet spectrum of factor A in ethanol shows only end absorption below 220 m$\mu$.

The nuclear magnetic resonance spectrum of A-28086 factor A in deuterochloroform showed the following characteristics: δ 6.01, 4.21, 4.11, 3.99, 3.89, 3.80, 3.67, 3.65, 3.57, 3.55, 2.83, 2.76, 2.74, 2.68, 2.66, 2.58, 2.56, 2.30, 2.22, 2.17, 2.10, 2.05, 1.96, 1.90, 1.85, 1.70, 1.62, 1.60, 1.47, 1.39, 1.31, 1.25, 1.18, 0.95, 0.93, 0.90, 0.88, 0.85, 0.77, 0.75, 0.73, 0.68, and 0.66 ppm.

Antibiotic A-28086 factor A, crystallized from acetone-water, has the following characteristic X-ray powder diffraction pattern ($Cu^{++}$ radiation, 1.5404λ, nickel filter, d = interplanar spacing in angstroms):

| d | Relative Intensity |
|---|---|
| 12.00 | 100 |
| 10.10 | 50 |

-continued

| d | Relative Intensity |
|---|---|
| 9.25 | 90 |
| 8.00 | 40 |
| 7.50 | 15 |
| 6.92 | 90 |
| 6.40 | 40 |
| 5.98 | 05 |
| 5.68 | 15 |
| 5.20 | 40 |
| 4.98 | 40 |
| 4.62 | 40 |
| 4.21 | 20 |
| 3.48 | 10 |

The specific rotation of antibiotic A-28086 factor A is −54° (c=0.2, methanol), when determined at a temperature of 25° C. This specific rotation is an average value, based on several determinations.

Electometric titration of factor A in 80 percent aqueous dimethylformamide indicated the presence of a titratable group with a $pK_a$ value of 7.9.

Antibiotic A-28086 factor A is soluble in a variety of organic solvents such as methanol, ethanol, dimethylformamide, dimethyl sulfoxide, ethyl acetate, chloroform, acetone, and benzene; but is only slightly soluble in non-polar organic solvents such as hexane; and is insoluble in water.

Antibiotic A-28086 factor A has an acid function capable of forming salts and ester derivatives and at least one hydroxyl group capable of esterification.

Antibiotic A-28086 factor B is a white crystalline compound (from acetone-water) which has a melting point of about 150°–153° C.

As determined by high-resolution mass spectrometry, factor B has an apparent molecular weight of 762 and a proposed empirical formula of $C_{43}H_{70}O_{11}$.

The infrared spectrum of factor B in chloroform has the following observed absorption maxima. 2.82, 3.30, 5.77, 5.85, 6.80, 7.20, 7.50 (weak), 7.72 (weak), 7.80 (weak), 8.57 (strong), 8.68, 8.90 (strong), 9.10, 9.50, 9.83 (strong), 9.90, 10.10, 10.17 (strong), 10.43 (weak), 10.80 (weak), 11.20 (weak), 11.35 (weak), 11.73 (weak), and 12.03 (weak) microns.

The ultraviolet spectrum of factor B in ethanol shows an absorption maximum at 220 mμ ($E_{1cm}^{1\%} = 137.5$; ε=10,477).

The nuclear magnetic resonance spectrum of A-28086 factor B in deuterochloroform showed the following characteristics: δ 7.20, 7.09, 6.26, 6.15, 4.19, 4.12, 4.05, 3.95, 3.89, 3.78, 3.62, 3.59, 3.52, 3.48, 2.81, 2.73, 2.63, 2.54, 2.52, 1.99, 1.91, 1.84, 1.71, 1.67, 1.64, 1.55, 1.43, 1.33, 1.18, 1.11, 0.96, 0.94, 0.90, 0.87, 0.84, 0.77, 0.74, and 0.68 ppm.

Antibiotic A-28086 factor B is soluble in a variety of organic solvents such as, for example, methanol, ethanol, dimethylformamide, dimethyl sulfoxide, ethyl acetate, chloroform, acetone and benzene; but is only slightly soluble in nonpolar organic solvents such as hexane; and is insoluble in water.

Antibiotic A-28086 factor D, when produced by S. aureofaciens NRRL 5758, is a minor factor. When produced by S. aureofaciens NRRL 8092, however, A-28086 factor D is present in amounts up to 10 percent of the recovered antibiotic activity. Antibiotic A-28086 factor D is the subject of a copending application of Nakatsukasa and Hamill, tilted ANTIBIOTIC A-28086 FACTOR D AND PROCESS FOR PRODUCTION THEREOF, Ser. No. 569,719, filed Apr. 21, 1975 now abandoned.

The following paragraphs describe the physical and spectral properties of antibiotic A-28086 factor D.

Antibiotic A-28086 factor D is a white crystalline material (from water-acetone) with a melting point of about 96°–98° C. A-28086 factor D has an apparent molecular weight of 778, as determined by high-resolution mass spectrometry.

The elemental composition of the peak in the mass spectrum of the sodium salt of A-28086 factor D was observed to be 800.5050 (Calcd for $C_{44}H_{73}O_{11}Na = 800.505$). In the mass spectrum of A-28086 factor D free acid, a small peak at 778 and a larger peak at 760.5117 (Calcd for $C_{44}H_{72}O_{10} = 760.5125$) were observed. The m/e 760 in the mass spectrum of the free acid results from the loss of water from the molecular ion. The molecular-ion composition of A-28086 factor D free acid is, therefore, $C_{44}H_{74}O_{11}$.

The empirical formula proposed for A-28086 factor D is $C_{44}H\theta O_{11}$. Elemental analysis of factor D gave the following percentage composition; carbon, 67.59 percent; hydrogen 9.38 percent; oxygen, 22.77 percent.

The theoretical percentage composition for $C_{44}H_{74}O_{11}$ is: carbon, 67.87 percent; hydrogen, 9.51 percent; oxygen, 22.77 percent.

The infrared absortpion spectrum of A-28086 factor D contains the following observable absorption maxima: 2.89, 3.39, 3.43, 3.50, 5.88, 6.90, 7.27, 7.60, 7.84, 9.00, 9.26, 9.62, 10.31, 10.58, 11.10, and 11.49 microns.

A-28086 factor D in 95 percent aqueous ethanol shows no ultraviolet absorption.

The nuclear magnetic resonance spectrum of A-28086 factor D in deuterochloroform showed the following characteristics: δ 6.00, 4.20, 4.10, 4.00, 3.98, 3.92, 3.86, 3.83, 3.79, 3.67, 3.64, 3.57, 3.54, 2.88, 2.81, 2.71, 2.62, 2.58, 2.48, 2.43, 2.37, 2.29, 2.21, 2.15, 2.10, 2.04, 1.97, 1.89, 1.83, 1.76, 1.68, 1.61, 1.58, 1.55, 1.47, 1.39, 1.30, 1.25, 1.18, 0.95, 0.90, 0.88, 0.84, 0.74, and 0.68 ppm.

Antibiotic A-28086 factor D, crystallized from acetone-water, has the following characteristic X-ray powder-diffraction pattern ($Cu^{++}$ radiation, 1.5405λ, nickel filter, d = interplanar spacing in angstroms):

| d | Relative Intensity |
|---|---|
| 12.40 | 100 |
| 10.20 | 70 |
| 8.85 | 90 |
| 7.80 | 30 |
| 6.80 | 10 |
| 6.30 | 100 |
| 5.70 | 20 |
| 5.35 | 20 |
| 5.10 | 20 |
| 4.90 | 10 |
| 4.65 | 20 |
| 4.45 | 40 |
| 4.20 | 30 |
| 3.30 | 10 |
| 3.15 | 10 |
| 2.99 | 05 |
| 2.77 | 05 |
| 2.28 | 05 |

The specific rotation of antibiotic A-28086 factor D is −56° (c = 0.1, methanol), when determined at a temperature of 25° C.

Electrometric titration of A-28086 factor D in 80 percent aqueous dimethylformamide indicated the presence of a titratable group with a $pK_a$ value of 8.67.

Antibiotic A-28086 factor D is soluble in a variety of organic solvents such as methanol, ethanol, dimethylformamide, dimethyl sulfoxide, ethyl acetate, chloroform, acetone and benzene. A-28086 factor D is only slightly soluble in nonpolar organic solvents such as hexane and is insoluble in water.

Antibiotic A-28086 factor D has an acid function capable of forming salts and ester derivatives and at least one hydroxyl group capable of esterification.

Antibiotic A-28086 factors A and B and certain acyl ester derivatives of factor A are capable of forming physiologically-acceptable salts with the alkali-metals, the alkaline-earth metals; and with amines. "Physiologically acceptable" salts are salts which are also pharmaceutically acceptable, that is, salts in which the toxicity of the compound as a whole toward warm-blooded animals is not increased relative to the non-salt form. Representative and suitable alkali-metal and alkaline-earth-metal salts of A-28086 factors A and B include the sodium, potassium, lithium, cesium, rubidium, barium, calcium, and magnesium salts. Suitable amine salts of A-28086 factors A and B include the ammonium and the primary, secondary and tertiary $C_1$–$C_4$-alkylammonium and hydroxy-$C_2$–$C_4$-alkylammonium salts. Illustrative amine salts include those formed by reaction of A-28086 factors A and B with ammonium hydroxide, methylamine, sec-butylamine, isopropylamine, diethylamine, diisopropylamine, ethanolamine, triethylamine, 3-amino-1-propanol and the like.

The alkali-metal and alkaline-earth-metal cationic salts of A-28086 factors A and B are prepared according to procedures commonly employed for the preparation of cationic salts. For example, the free acid form of the antibiotic factor is dissolved in a suitable solvent such as warm methanol or ethanol; a solution containing the stoichiometric quantity of the desired inorganic base in aqueous methanol is added to this solution. The salt thus formed can be isolated by routine methods, such as filtration or evaporation of the solvent.

The salts formed with organic amines can be prepared in a similar manner. For example, the gaseous or liquid amine can be added to a solution of the antibiotic factor in a suitable solvent such as acetone, and the solvent and excess amine can be removed by evaporation.

It is well known in the veterinary pharmaceutical art that the form of an antibiotic is not significant when treating an animal with the antibiotic. In most cases, conditions within the animal change the drug to forms other than the form in which it was administered. The salt form in which it may be administered is, therefore, insignificant to the method of treatment. The salt form may, however, be chosen for reasons of economics, convenience, and toxicity.

The A-28086 antibiotics are produced by culturing an A-28086-producing strain of *Streptomyces aureofaciens* under submerged aerobic conditions in a suitable culture medium until substantial antibiotic activity is produced. The antibiotics are recovered by employing various isolation and purification procedures commonly used and understood in the art.

One of the A-28086-producing organisms is identified as *S. aureofaciens* NRRL 5758, and is classified as a strain of *Streptomyces aureofaciens* Duggar.

A second A-28086-producing organism was derived from *S. aureofaciens* NRRL 5758 by a series of natural selections, followed by chemical mutation. This organism, identified as NRRL 8092, is also classified as a strain of *Streptomyces aureofaciens* Duggar.

The culture medium employed to grow *Streptomyces aureofaciens* NRRL 5758 or *Streptomyces aureofaciens* NRRL 8092 can be any one of a number of media. For economy in production, optimal yield, and ease of product isolation, however, certain culture media are preferred. Thus, for example, preferred carbohydrate sources in large-scale fermentation are tapioca dextrin and sucrose, although glucose, corn starch, fructose, mannose, maltose, lactose, and the like can also be employed. Corn oil, peanut oil, soybean oil and fish oil are other useful sources of carbon. A preferred nitrogen source is enzyme-hydrolyzed casein, although peptones, soybean meal, cotton-seed meal, amino acids such as glutamic acid, and the like are also useful. Among the nutrient inorganic salts which can be incorporated in the culture media are the customary soluble salts capable of yielding sodium, magnesium, calcium, ammonium, chloride, carbonate, sulfate, nitrate, and like ions.

Essential trace elements necessary for the growth and development of the organism should also be included in the culture medium. Such trace elements commonly occur as impurities in other constitutents of the medium in amounts sufficient to meet the growth requirements of the organism.

It may be necessary to add small amounts (i.e. 0.2 ml/l.) of an antifoam agent such as polypropylene glycol to large-scale fermentation media if foaming becomes a problem.

Although it is not essential, the antibiotic production of the A-28086-producing *Streptomyces aureofaciens* strains is enhanced by the addition of a small amount of oil such as soybean oil.

For production of substantial quantities of the A-28086 antibiotics, submerged aerobic fermentation in tanks is preferred. Small quantities of the A-28086 antibiotics may be obtained by shake-flask culture. Because of the time lag in antibiotic production commonly associated with innoculation of large tanks with the spore form of the organism, it is preferable to use a vegetative inoculum. The vegetative inoculum is prepared by inoculating a small volume of culture medium with the spore form of mycelial fragments of the organism to obtain a fresh, actively growing culture of the organism. The vegetative inoculum is then transferred to a larger tank. The medium used for the growth of the vegetative inoculum can be the same as that employed for larger fermentations, but other media can also be employed.

The A-28086-producing organisms can be grown at temperatures between about 20° and 40° C. Optimum A-28086 production appears to occur at temperatures of about 27°–30° C.

As is customary in aerobic submerged culture processes, sterile air is blown through the culture medium. For efficient growth of the organism the volume of air employed in the tank production is preferably above 0.1 volume of air per volume of culture medium per minute. For efficient production of A-28086 antibiotics the volume of air employed in the tank production is preferably above 0.25 volume of air per volume of culture medium per minute. High levels of dissolved oxygen do not depress antibiotic production.

The production of these A-28086 antibiotics can be followed during the fermentation by testing samples of the broth or of extracts of te mycelial solids for antibiotic activity against organisms known to be sensitive to the antibiotics. One assay organism useful in testing the A-28086 antibiotics is *Bacillus subtilis* ATCC 6633. The bio-assay is conveniently performed by paper-disc assay on agar plates.

The initial pH of the uninoculated culture medium varies with the medium used. In general, the pH should be in the range of 6.0 to 7.5. The harvest pH at the end of the fermentation is usually slightly higher, in the range of 6.5 to 8.0.

Generally, antibiotic activity is detachable on the second day of the fermentation. Maximum production of antibiotic activity usually occurs between about the sixth and the tenth days.

Following their production under submerged aerobic fermentation conditions, the A-28086 antibiotics previously described can be recovered from the fermentation medium by methods commonly employed in the fermentation art. The antibiotic activity produced during fermentation of an A-28086-producing organism occurs in both the mycelial mass and the the filtered broth. Maximum recovery of the A-28086 antibiotics is accomplished, therefore, by a combination of methods, including filtration, extraction, and adsorption chromatography. A preferred solvent for separating the A-28086 antibiotics from either whole or filtered fermentation broth is ethyl acetate, although other commonly used solvents are satisfactory.

An especially advantageous method of separating the A-28086 factors A, B and D is to lower the pH of the whole fermentation broth to about pH 3.0. At this pH 3.0 the A-28086 factors A, B, and D are conveniently separated with the mycelial mass by filtration. This method is the subject of a copending application of Boeck and Berg titled ANTIBIOTIC RECOVERS PROCESS, Ser. No. 569,712, filed Apr. 21, 1975. Another advantageous method of separating the A-28086 factors involves adding a bicarbonate such as, for example, sodium bicarbonate, to the whole broth in amounts of approximately one gram per liter. The A-28086 factors are, thereby, conveniently separated with the mycelial mass in salt form. Methanol is a preferred solvent for separating the antibiotics from the mycelial mass, but other lower alcohols and ketones are also suitable.

Azeotropic distillation can also be advantageously employed in the recovery of the A-28086 antibiotics. In this method an organic solvent which forms an appropriate azeotrope with water is added to the aqueous fermentation broth. This solvent-broth mixture is subjected to azeotropic distillation in order to remove at least half the water from the broth, leaving a water-solvent mixture in which the A-28086 antibiotics are in solution in the organic solvent. Insoluble by-products can be separated by suitable means such as filtration or centrifugation. The A-28086 antibiotics can then be recovered from the organic solution by well-known procedures such as evaporation of solvent, precipitation by adding a nonsolvent, or extraction.

Organic solvents which form appropriate azeotropes with water in order to carry out such a recovery procedure include, illustratively, butyl alcohol, amyl alcohol, hexyl alcohol, benzyl alcohol, butyl acetate, amyl acetate, 1,2-dichloroethane, 3-pentanone, 2-hexanone, benzene, cyclohexanone, toluene, the xylenes and the like.

There is special advantage in recovery by azeotropic distillation on large-scale fermentation processes. Both water and solvent taken overhead in the azeotrope can be separated by known techniques and thereafter recycled for further use. The water thus removed is free of contaminants and does not require a waste disposal process. The solvent thus removed may be recycled to the process.

Further purification of the A-28086 antibiotics includes additional extraction and adsorption procedures. Adsorptive materials such as silica gel, carbon, Florisil (magnesium silicate, Floridin Co., P.O. Box 989, Tallahassee, Fla.) and the like can be advantageously employed.

Alternatively, the culture solids, including medium constituents and mycelium can be used without extraction or separation, but preferably after removal of water, as a source of the A-28086 antibiotics. For example, after production of A-28086 antibiotic activity, the culture medium can be dried by lyophilization and mixed directly into feed premix.

In another aspect, after production of A-28086 activity in the culture medium, the mycelium can be separated and dried to give a product which can be used directly in a feed premix. When separating the mycelium for such use, the addition of calcium carbonate (about 10 g./l.) aids in filtration and gives an improved dried product.

Under the conditions employed thus far, the *Streptomyces aureofaciens* strains described previously and designated as NRRL 5758 and NRRL 8092 produce antibiotic A-28086 factor A as the predominant factor. Although the ratio of factors varies depending on the fermentation conditions used, in general factor A accounts for more than 99 percent of the total recovered antibiotic activity from NRRL 5758 and for about 90 percent of the total recovered antibiotic activiy from NRRL 8092. A-28086 factor B accounts for most of the remaining antibiotic activity from NRRL 5758, and factor D is a minor factor. On the other hand, A-28086 factor D accounts for about 8–10 percent of the total recovered antibiotic activity from NRRL 8092, and factor B is a minor factor.

Antibiotic A-28086 factors A, B, and D are separated from each other and are isolated as individual compounds by the use of well-known methods such as column chromatography, thin-layer chromatography and the like. For example, column chromatography over silica gel is used to separate factors A, B, and D by eluting the column with varying solvent mixtures, such as benzene-ethyl acetate. Using benzene-ethyl acetate solvent mixtures over a silica gel column, factor B is eluted first, and factors A and D are eluted later. Thin-layer chromatography, as described hereinabove, is a convenient method for monitoring elution progress.

The preparation of A-28086 antibiotics and the separation and purification of the antibiotic factors, together with preparation of salts of the antibiotics are exemplified hereinbelow.

EXAMPLE 5

A. Shake-flask Fermentation of A-28086 using *S. aureofaciens* NRRL 5758

A culture of *Streptomyces aureofaciens* NRRL 5758 was prepared and maintained on an agar slant having the following composition:

| Ingredient | Amount |
|---|---|
| Agar | 20 g |
| Dextrin | 10 g |
| Enzyme-hydrolyzed casein | 2 g |
| Beef extract | 2 g |
| Yeast extract | 2 g |
| Distilled water | q.s. 1 liter |

The slant was inoculated with *Streptomyces aureofaciens* NRRL 5758, and the inoculated slant was incubated at 30° C. for 6 to 10 days. The mature slant culture was covered with beef serum, and scraped with a sterile loop to loosen the spores. The resulting beef-serum suspension of spores and mycelial fragments was lyophilized into six pellets.

One lyophilized pellet thus prepared was used to inoculate 50 ml of a vegetative medium having the following composition:

| Ingredient | Amount |
|---|---|
| Glucose | 20 g |
| Soybean grits | 15 g |
| Corn-steep liquor | 10 g |
| $CaCO_3$ | 2 g |
| Tap Water | q.s. 1 liter |

The inoculated vegetative medium, in a 250-ml Erlenmeyer flask, was incubated at 30° C. for 72 hours on a shaker rotating through an arc 2 inches in diameter at 250 rpm.

B. Tank Fermentation of A-28086 using *S. aureofaciens* NRRL 5758

In order to provide a larger volume of inoculum, 10 ml of the incubated vegetative medium described above was used to inoculate 400 ml of a second-stage vegetative growth medium having the same composition as that of the vegetative medium. This second-stage medium, in a 2-liter flask, was incubated at 30° C. for 24 hours on a shaker rotating through an arc 2 inches in diameter at 250 rpm.

This second-stage vegetative medium (1 l.) was used to inoculate 100 liters of sterile production medium of the following composition:

| Ingredient | Amount |
|---|---|
| Tapioca dextrin* | 60.0 g/l. |
| Enzyme-hydrolyzed casein** | 8.0 g/l. |
| Molasses | 15.0 g/l. |
| $MgSO_4 \cdot 7H_2O$ | 0.5 g/l. |
| $CaCO_3$ | 2.0 g/l. |
| Refined soybean oil | 5.0 g/l. |
| Deionized water | g.s. 1 liter |

*Staley Dextrin No. 11, A. E. Staley Co., Decatur, Ill.
**Amber EHC, Amber Laboratories, Juneau, Wisc.

The pH of the medium was 6.7 after sterilization by autoclaving at 120° C. for 30 minutes at 15–20 pounds pressure. In a 165-liter fermentation tank, the inoculated production medium was allowed to ferment for 10 days at a temperature of 29° C. The fermentation medium was aerated with sterile air at the rate of 0.4 volumes of air per volume of culture medium per minute. The medium was stirred with conventional agitators at 250 rpm.

EXAMPLE 6

The A-28086 antibiotics were also produced according to the process of Example 5, but utilizing a flask-production medium having the following composition:

| Ingredient | Amount |
|---|---|
| Glucose | 10 g/l. |
| Edible molasses | 20 g/l. |
| Peptone | 5 g/l. |
| $CaCO_3$ | 2 g/l. |
| Tap water | q.s. 1 liter |

EXAMPLE 7

Separation of the A-28086 Antibiotic Complex Produced by *S. aureofaciens* NRRL 5758

Whole fermentation broth (132 l.), obtained by the method described in Example 5, was filtered with a filter aid (Hyflo Super-cel, a diatomaceous earth, Johns-Manville Products Corp.) to give 97 liters of filtered broth. The filtered broth was extracted with an approximately equal volume of ethyl acetate. The ethyl acetate extract was separated from the aqueous phase and was concentrated to a volume of about 500 ml. This concentrated ethyl acetate extract was added to a large excess of petroleum ether (Skelly Solve F; about 10 l.) to precipitate and, thereby, separate unwanted material. The separated filtrate was evaporated under vacuum to give the broth portion of A-28086 antibiotic complex (6.9 g).

The mycelial portion of A-28086 antibiotic complex was obtained by extracting the filtered mycelium twice with approximately half volumes of methanol (62 l. and 59 l.). The two methanol extracts were combined and were concentrated under vacuum to remove the methanol. After this concentration about 10 l. of an aqueous phase remained. This aqueous phase was adjusted to about pH 7.5 with dilute sodium hydroxide. The resulting solution was extracted twice with approximately equal volumes of ethyl acetate (9 l. and 10 l.). The ethyl acetate extracts were combined and then concentrated to a volume of about 400 ml. This concentrated ethyl acetate extract was added to a large excess of petroleum ether to remove unwanted materials, using the procedure described above for the concentrated filtered broth extract. The mycelial portion of A-28086 antibiotic complex obtained from the filtrate weighed 20.6 g.

Example 8

Isolation of A-28086 Individual Factors A and B

The mycelial portion of A-28086 antibiotic complex (235 g, prepared as described in Example 7) was dissolved in about 80 ml of benzene. This benzene solution was applied to a silica gel column (9 × 130 cm, 8

1., Matheson grade 62 silica gel). The column was eluted with varying benzene-ethyl acetate mixtures. Elution progress was followed by thin-layer chromatography. Using a benzene-ethyl acetate (90:10) solvent system, factor B was eluted first and was isolated as an individual factor. Factor B (43 mg) was crystallized from acetone-water, m.p. 150°–153° C.

Continuing to elute with benzene-ethyl acetate mixtures, but gradually increasing the ratio of ethyl acetate present, factor A was eluted; the various fractions containing factor A were combined and were concentrated under vacuum to a residue. This residue was dissolved in acetone (about 150 ml); water (about 150 ml) was added to the acetone solution. The pH of the resulting solution was adjusted to pH 3 by the addition of 1 N hydrochloric acid. The acidified mixture was stirred about one hour, during which time a precipitate formed. This precipitate was separated by filtration and was recrystallized from acetone (about 150 ml) upon addition of water (about 60 ml). The product was dried overnight under vacuum to give factor A (about 6.6 g). After partial evaporation of acetone from the filtrate, a second crop of factor A (about 1.2 g) was obtained.

EXAMPLE 9

Preparation of A-28086 Factor A Sodium Salt

Antibiotic A-28086 factor A (500 mg) was dissolved in acetone (50 ml.) Water (50 ml) was added to this solution, and 5 N sodium hydroxide was added to bring the pH of the solution to 10.5–11. The resulting solution was stirred for one hour and then was extracted with ethyl acetate. The ethyl acetate extract was evaporated to dryness under vacuum. The residue was precipitated from an acetone-water solution to give 378 mg of A-28086 factor A sodium salt, melting point 120°–123° C.

EXAMPLES 10–13

Antibiotic A-28086 factor A barium salt was prepared from antibiotic A-28086 factor A (500 mg) and saturated barium hydroxide, using the method of Example 9 to give 369 mg of A-28086 factor A barium salt, melting point 188°–190° C.

Antibiotic A-28086 factor A potassium salt was prepared from antibiotic A-28086 factor A (500 mg) and 5 N potassium hydroxide, using the method of Example 9 to give 363 mg of A-28086 factor A potassium salt, melting point 165°–167° C.

Antibiotic A-28086 factor A cesium salt was prepared from antibiotic A-28086 factor A (500 mg) and 1 N cesium hydroxide, using the method of Example 9 to give 540 mg of A-28086 factor A cesium salt, melting point 190°–210° C.

Antibiotic A-28086 factor B sodium salt, prepared from antibiotic A-28086 factor B and 5 N sodium hydroxide according to the method of Example 9.

EXAMPLE 14

Shake-flask Fermentation of A-28086 using *S. aureofaciens* NRRL 8092

A culture of *Streptomyces aureofaciens* NRRL 8092 was prepared and maintained on an agar slant having the following composition:

| Ingredient | Amount |
| --- | --- |
| $K_2HPO_4$ | 2 g |
| $MgSO_4 \cdot 7H_2O$ | 0.25 g |
| $NH_4NO_3$ | 2 g |
| $CaCO_3$ | 2.5 g |
| $FeSO_4 \cdot 7H_2O$ | 0.001 g |
| $MnCl_2 \cdot 7H_2O$ | 0.001 g |
| $ZnSO_4 \cdot 7H_2O$ | 0.001 g |
| Glucose | 10 g |
| Agar | 20 g |
| Deionized water | q.s. 1 liter |
| pH (unadjusted) | 7.7 |

The slant was inoculated with *Streptomyces aureofaciens* NRRL 8092, and the inoculated slant was incubated at 30° C. for about 7 days. The mature slant culture was covered with sterile beef serum and was scraped with a sterile loop to prepare a spore and mycelial suspension from the slant culture. The resulting suspension was lyophilized into a maximum of six pellets.

One of the lyophile pellets thus prepared was used to inoculate 50 ml of a vegetative medium having the following composition:

| Ingredient | Amount |
| --- | --- |
| Glucose | 20 g |
| Soybean flour | 15 g |
| Corn-steep liquor | 10 g |
| $CaCO_3$ | 2 g |
| Tap water | q.s. 1 liter |

The inoculated vegetative medium, in a 250-ml Erlenmeyer flask, was incubated at 30° C. for 48 hours on a rotary shaker at 250 rpm with a 2-inch arc.

The incubated vegetative medium described above (0.5 ml, 1 percent) was used to inoculate 50 ml of a fermentation medium having the following composition:

| Ingredient | Amount |
| --- | --- |
| Tapioca dextrin | 60.0 g |
| Enzyme-hydrolyzed casein | 6.0 g |
| Enzymatic hydrolysate of casein*** | 2.0 g |
| $CaCO_3$ | 2.0 g |
| $MgSO_4 \cdot 7H_2O$ | 0.5 g |
| Blackstrap molasses | 15.0 g |
| Refined soybean oil | 5.0 ml |
| Tap water | q.s. 1 liter |
| pH (unadjusted) 6.6 | |

***NZ Amine A, Sheffield Chemical Co., Norwich, N.Y.

EXAMPLE 15

Tank Fermentation of A-28086 using *S. aureofaciens* NRRL 8092

The initial procedure described in Example 14 for the shake-flask fermentation A-28086 was also used for tank fermentation. In order to produce a larger volume of inoculum, 10 ml of the incubated vegetative medium was used to inoculate 400 ml of a second-stage vegetative medium having the same composition as that of the first vegetative medium. This second-stage medium, in a 2-liter Erlenmeyer flask, was incubated at 30° C. for 24 hours on a rotary shaker at 250 rpm with a 2-inch arc.

This incubated second-stage vegetative medium (800 ml) was used to inoculate 100 liters of sterile fermentation medium having the following composition:

| Ingredient | Amount |
| --- | --- |
| Tapioca dextrin | 60.0 g/l. |
| Enzyme-hydrolyzed casein | 6.0 g/l. |
| Enzymatic-hydrolysate of casein | 2.0 g/l. |
| $CaCO_3$ | 2.0 g/l. |
| $MgSO_4 \cdot 7H_2O$ | 0.5 g/l. |
| Blackstrap molasses | 15.0 g/l. |
| Refined soybean oil | 5.0 mg/l. |
| Tap water | q.s. 1 liter |

The pH of the medium was 6.8 ± 0.1 after sterilization by autoclaving at 121° C. for 30 minutes at 15–20 pounds pressure. In a 165-liter fermentation tank the inoculated production medium was allowed to ferment for 10–12 days at 28 ± 1° C. The fermentation medium was aerated with sterile air at the rate of 0.4 volumes of air per volume of culture medium per minute. The medium was stirred with conventional agitators at 300 rpm.

EXAMPLE 16

Separation of the A-28086 Antibiotic Complex Produced by *S. aureofaciens* NRRL 8092

Whole fermentation broth (60 liters), obtained by the method described in Example 15, was adjusted to pH 3 by the addition of dilute HCl. The resulting solution was filtered using a filter aid (Hyflo Super-cel, a diatomaceous earth, Johns-Manville Products Corp.). The separated mycelial cake was extracted with 30 liters of methanol, adding 1.56 kg of $NaHCO_3$ to the extract with stirring. After separation of this extract, the mycelial cake was again extracted with another 30 liters of methanol. The two methanol extracts were combined and concentrated under vacuum to remove the methanol. The remaining aqueous solution (about 7 liters) was adjusted to pH 7.5 with dilute HCl. The resulting solution was extracted twice with ethyl acetate (7-liter portions). The ethyl acetate extracts were combined and concentrated under vacuum to give an oily residue. This oily residue was dissolved in 1500 ml of acetone. Water (1500 ml) was added to the acetone solution. The resulting solution was adjusted to pH 3 with dilute HCl and was stirred 1 hour. The precipitate which had formed was separated by filtration and then was dissolved in acetone (1500 ml); water (400 ml) was added to this solution. The resulting solution was allowed to stand for 16 hours for crystallization to occur. The crystals formed were separated by filtration and dried under vacuum to give 74 g crude crystalline product containing A-28086 factors A and D and other crystalline impurities.

This crude crystalline product (40 g) was dissolved in about 250 ml of benzene. The benzene solution was then applied to a silica-gel column (9- × 120-cm column; Grace-Davidson grade 62 silica gel). The column was eluted successively with 40 liters of each of the following:

| | |
| --- | --- |
| 1) | benzene |
| 2) | benzene:ethyl acetate (9:1) |
| 3) | benzene:ethyl acetate (4:1) |
| 4) | benzene:ethyl acetate (7:3) |
| 5) | benzene:ethyl acetate (1:1) |
| 6) | ethyl acetate |
| 7) | methanol |

One-liter fractions were collected. Each fraction was checked by assay against *Bacillus subtilis* and by thin layer chromatography to identify the eluted compounds. A-28086I was eluted with benzene:ethyl acetate (4:1). A-28086 factor B was eluted with benzene:ethyl acetate (7:3). A-28086 factors A and D were eluted in the fractions obtained with benzene:ethyl acetate (7:3 and 1:1), fractions 119–156. These fractions were combined and evaporated to dryness under vacuum. The residue thus obtained was dissolved in acetone (500 ml). Water (500 ml) was added to the acetone solution, and the resulting solution was adjusted to pH 3 with dilute HCl and was stirred for one hour. The precipitate which formed was separated by filtration and was crystallized from acetone (500 ml)-water (180 ml.). The crystals thus formed were separated by filtration and dried under vacuum to give 20.1 g of a mixture of A-28086 factors A and D.

EXAMPLE 17

Separation and Purification of Individual Factors A and D

The crystalline mixture of A-28086 factors A and D obtained in Example 16 (18.8 g) was dissolved in benzene (50 ml). The benzene solution was applied to a silica-gel column (7- × 100-cm column; E. Merck grade 60 silica gel, finer than 230 mesh ASTM). The column was eluted at a flow rate of 90 ml per hour, successively with:

1. 12 liters of benzene
2. 12 liters of benzene:ethyl acetate (9:1)
3. 12 liters of benzene:ethyl acetate (4:1)
4. 32 liters of benzene:ethyl acetate (7:3)
5. 10 liters of methanol Thin-layer cellulose chromatography (Merck Darmstadt cellulose on aluminum support) was followed by *B. subtilis* bioautography to monitor the elution procedure. The following solvent system was used: water:methanol:acetone (12:3:1), adjusting the solution first to pH 10.5 with $NH_4OH$ and then to pH 7.5 with HCl.

One- to two-liter fractions were collected until activity was detected; then 200-ml fractions were collected. The fractions containing only A-28086 factor D were combined and evaporated under vacuum to a residue. This residue crystallized from acetone-water (1:1). The crystals were separated and dried under vacuum to give 140 mg of crystalline A-28086 factor D.

The fractions containing A-28086 factor D with a trace of A-28086 factor A were treated in the same manner to give an additional 150 mg of crystalline A-28086 factor D containing a small amount of A-28086 factor A.

Carbomonensin, or metabolite A-27106, is obtained by reaction of a mixture of the antibiotic monensin, or the mycelial culture in which monensin is produced, and glucose, with an enzyme system produced by submerged aerobic culture of a strain of *Streptomyces candidus*. A culture of this strain has been placed on deposit, without restriction as to availability, with the permanent culture collection of the U.S. Department of Argriculture, Norther Regional Research Laboratory, Peoria, Illinois 61604, where the culture was assigned the accession number NRRL 5449.

The culture medium employed to grow *S. candidus* NRRL 5449 can be any one of a number of media. However, for economy in production, optimal yield, and ease of product isolation, certain culture media are preferred. Thus, for example, among the preferred sources of carbohydrate in large-scale fermentation are invert sugar or corn syrup, although glucose, fructose, maltose, starch, inositol, and the like can also be employed. When monensin is to be converted to metabolite A-27106 in fermentation culture at the time *S. candidus* NRRL 5449 is grown, the medium must contain a source of glucose to achieve efficient conversion. When *S. candidus* NRRL 5449 is grown to produce its enzyme system for later use in converting monensin to metabolite A-27106, the presence of glucose during fermentation is optional. Preferred sources of nitrogen are peptones, soybean meal, amino acid mixtures and the like. Among the nutrient inorganic salts which can be incorporated in the culture media are the customary soluble salts capable of yielding iron, sodium, potassium, ammonium, calcium, phosphate, chloride, carbonate, and like ions.

Essential trace elements necessary for the growth and development of the organism should also be included in the culture medium. Such trace elements commonly occur as impurities in other constituents of the medium in amounts sufficient to meet the growth requirements of the organism.

The initial pH of the culture medium can be varied. Prior to inoculation with the organism, however, it is desirable to adjust the pH of the culture medium to between about pH 5.7 and about pH 7.5, depending upon the particular medium employed. As is the case with other Actinomycetes, the medium gradually becomes more alkaline as the fermentation proceeds and may rise from an initial pH of about pH 5.9 to about pH 6.9 or higher during the growth period of the organism. The final pH is controlled, at least in part, by the initial pH of the medium, the buffers present in the medium, and the duration of time the organism is permitted to grow. Although pH can be adjusted by addition of either acid or base, good results have been achieved with no adjustment of pH.

In common with other *Streptomyces species, organism NRRL* 5449 requires aerobic growth conditions. Small-volume propagation is conveniently carried out on agar slants or plates, in shake flasks or in bottles. For large-scale production, submerged aerobic culture in large tanks is preferred.

The fermentation medium in a sterile tank can be inoculated with a sporulated suspension to initiate fermentation. However, since inoculation with a sporulated suspension involves a growth lag, a vegetative inoculum is preferable. The vegetative inoculum is prepared by inoculating a small volume of culture medium with the spore form or mycelial fragments of the organism to obtain a fresh, actively growing culture of the organism. The vegetative inoculum is then transferred to a larger tank. The medium used for the growth of the vegetative inoculum can be the same as that used for large-scale production, but other media can be employed.

The organism *S. candidus* NRRL 5449 will grow over a temperature range between about 26° C. to about 40° C. Maximum growth and sporulation, however, occur between about 32° C. and about 37° C.

As is customary in aerobic submerged culture processes, sterile air is blown through the culture medium during fermentation. For efficient growth of the organism and production of metabolite A-27106, the volume of air employed in tank production of the substance should be above about 0.1 volume of air per volume of culture medium per minute. Optimal yields are obtained when the volume of air used is at least one-third to one-half volume of air per volume of culture medium per minute.

The fermentation time needed to convert monensin to metabolite A-27106 varies. The presence of an adequate supply of glucose is essential for the conversion of monensin to metabolite A-27106. In general, when glucose is present in adequate amounts and monensin is present in about 0.1 to 1.0 grams per liter of medium, conversion of monensin to metabolite A-27106 is essentially complete by about 36 to 72 hours. Optimal conversion occurs when monensin is present in a range of from 0.5 to 0.7 grams per liter of medium. An adequate amount of glucose is above 2 percent of medium by weight. A preferred amount of glucose is from about 2.0 to about 2.5 percent of medium by weight. A glucose-sensing test paper may be used to check concentration levels. When glucose content drops below about two percent, glucose should be added to maintain concentration at optimum levels.

When the separated *S. candidus* enzyme system is used to effect conversion of monensin to metabolite A-27106, it is not essential that the enzyme preparation be highly purified. For example, filtered fermentation broth can be lyophilized and stored for at least as long as two weeks before reconstituting with an aqueous buffer, using approximatley one-sixth the volume of original broth. Efficient conversion is achieved after about 72 hours when 2.5 g. of such a lyophilized preparation is reconstituted in the presence of 25 mg. of monensin.

The active enzyme system is present in both the filtered broth and the cells. An enzyme system of greater purity can be obtained from the separated fermentation cells. These cells may be frozen and stored for periods at least as long as three months. The thawed cells can be then reconstituted by suspending them in a buffer solution. The buffer suspension is further purified by sonication and centrifugation. The purified cell debris thus separated is resuspended in buffer and is dialyzed. Using this method, 200 g. of cells from the fermentation medium give purified dialyzate sufficient to convert glucose and 25 mg. of monensin to metabolite A-27106.

Conversion progress can be monitored by thin-layer chromatography (tlc). On silica gel (F-254, E-N Laboratories, Inc., Elmsford, N. Y.) in benzene-methanol (7:3), the Rf valve for monensin is 0.62, whereas the Rf value for metabolite A-27106 sodium salt is 0.49. A vanillin spray reagent can be used for detection. This reagent is prepared by adding fuming sulfuric acid (2 ml.) to a solution of vanillin (3 g.) in absolute ethanol (100 ml.).

Metabolite A-27106 is present in both the culture broth and in the mycelia. Accordingly, techniques employed in the isolation of the metabolite are designed to permit maximum recovery of the product from either or both sources. Thus, for example, the fermentation medium is filtered, and both the filtrate and the mycelial cake are extracted with suitable solvents to obtain metabolite A-27106 as the sodium salt. The product is recovered from the extracting solvents by ordinary methods commonly employed in the art.

Alternatively, the culture solids, including medium constituents and mycelia, can be used without extraction or separation, but preferably with removal of water from the mycelia and culture medium, as a source of metabolite A-27106 sodium salt. For example, the culture medium cn be dried by lyophilization and mixed into feed. Also, the solids can be converted without total removal of water to a thin slurry which is suitable for addition to wet mash and similar feeds.

No single extraction/isolation procedure is mandatory. In one satisfactory manner, the finished culture medium is filtered, using a filter aid. The filter cake is extracted with a polar solvent such as methanol. The methanol extract is concentrated and then added to the original aqueous filtrate. This combined solution is extracted twice with half volumes of chloroform. The chloroform extracts are evaporated under vacuum to give a dark amber oil.

This oil is decolorized over an activated-charcoal column, using chloroform and about 20 g. of activated charcoal per gram of oil. The eluate is again concentrated under vacuum to give a pale yellow to colorless oil. This oil, dissolved in a minimal amount of chloroform, is chromatographed on a silica-gel column, using ethyl acetate as a solvent. Elution is monitored by thin-layer chromatography. Impurities are eluted with ethyl acetate. Elution with ethyl acetate-methanol mixtures affords metabolite A-27106 sodium salt.

Metabolite A-27106 sodium salt is a white crystalline solid, melting with bubbling at about 170°–175° C. Metabolite A-27106 sodium salt appears to form a hydrate or other solvate very rapidly. When A-27106 sodium salt is hydrated or solvated, its melting point varies, generally melting a few degrees below the indicated value.

Elemental analysis of metabolite A-27106 sodium salt gave the following percentage composition; carbon, 58.78; hydrogen, 8.51; oxygen, 27.85; and sodium, 3.63. These values correlate with empirical formula $C_{42}H_{71}O_{16}Na$ which has a theoretical percentage composition of carbon, 59.00; hydrogen, 8.37; oxygen, 29.94; and sodium, 2.42.

Metabolite A-27106 sodium salt exhibits practically no ultraviolet absorption above about 235μ.

The infrared absorption spectrum of metabolite A-27106 sodium salt in chloroform contains the following observable maxima: 3.1, 3.36, 6.39, 6.82, 7.1, 7.25, 7.9 (shoulder), 8.1, 8.3, 8.67, 8.8 (shoulder), 9.04, 9.22, 9.51, 9.66, 10.03, 10.26, 10.66, 11.23, 1147, 11.83, and 12.15.

The mass spectrum of metabolite A-27106 sodium salt shows a molecular-ion peak and other characteristic peaks as listed below:

| m/e Calcd. | Observed | Fragment |
|---|---|---|
| 854.46230 | 854.44630 | $C_{42}H_{71}O_{16}Na$ ($M^+$) |
| 836.45229 | 836.44129 | $C_{42}H_{69}O_{15}Na$ ($M^+ - H_2O$) |
| 779.45490 | 779.44690 | $C_{40}H_{68}O_{13}Na$ ($M^+ - [CH_3O \cdot +CO_2]$) |
| 761.44540 | 761.44740 | $C_{40}H_{66}O_{12}Na$ ($M^+ - [CH_3O \cdot +CO_2+H_2O]$) |

These findings confirm the assigned empirical formula and a molecular weight of 854 for metabolite A-27106 sodium salt.

In general, metabolite A-27106 sodium salt is readily soluble in highly polar solvents, is insoluble in nonpolar solvents, and varies in solubility in solvents of intermediate polarity. Illustratively, A-27106 sodium salt is soluble in lower aliphatic alcohols, is partially soluble in phenol, diethyl ether and acetone, and is relatively insoluble in liquid lower alkanes.

The acid form of metabolite A-27106 is a white amorphous solid, having a molecular weight of about 832. Electrometric titration of metabolite A-27106 (free acid) in water at an initial pH of 8 revealed the presence of a titratable group with a pKa value of 7.2.

The monosodium salt is, in general, the natural form of metabolite A-27106. From the sodium salt, the free acid is easily produced; from the free acid, the ammonium and other alkali-metal salts are prepared. The various metallic salts behave somewhat like alkali-metal carboxylates and somewhat like chelates.

In preparing another form, metabolite A-27106 sodium salt is dissolved in an aqueous solvent, such as methanol-water; an acid such as, for example, hydrochloric acid is added to lower the pH to 5 or below. The methanol is removed under vacuum, and the resulting aqueous acid product is extracted with chloroform. The chloroform extract is dried and evaporated to give metabolite A-27106, the free acid.

The free-acid form of metabolite A-27106 can be further modified by titrating it with an aqueous alkali-metal hydroxide or aqueous ammonia to obtain the corresponding lithium, potassium, rubidium, cesium or ammonium forms. Metabolite A-27106 and the ammonium and alkali-metal salts thereof are all biologically active.

The exact structure of metabolite A-27106 is not known. It is known that, in the conversion of monensin to metabolite A-27106, glucose is necessary and is consumed, even in the absence of metabolizing *S. candidus* cells. The molecular weight of A-27106 corresponds to that of a glucosyl monensin.

EXAMPLE 18

Preparation of A-27106 from Monensin by S. candidus

*S. candidus* NRRL 5449 was grown on an agar slant prepared from Bennett's medium to give a well-defined colony. The colony was removed and made up as a slurry with sterile deionized water (10 ml.).

This slurry was divided among four 500-ml. shake flasks, each containing 100 ml. of vegetative medium of the following composition

| Ingredient | Amount |
|---|---|
| Corn distillers' solubles* | 25. g. |
| Lactose | 10. g. |
| Maltose | 10. g. |
| $FeSO_4 \cdot 7H_2O$ | 0.01 g. |
| $MgSO_4 \cdot 7H_2O$ | 2. g. |
| $KH_2PO_4$ | 2. g. |
| $CaCO_3$ | 2. g. |
| Deionized water | q.s. 1.1 liter |

*Nadrisol, National Distiller's Products Company

The four inoculated flasks were incubated at 30° C. on a rotary shaker at 250 r.p.m. for 24 hours. This vegetative medium (10-ml. portions) was used to inoculate each of 15 shake flasks (500 ml.) containing 100 ml. of sterilized fermentation medium of the following composition:

| Ingredient | Amount |
| --- | --- |
| Beef extract | 5 g. |
| Casein pancreatic hydrolysate peptone | 5 g. |
| NaCl | 5 g. |
| Glycerol | 15 g. |
| CaCO$_3$ | 2 g. |
| Deionized water | q.s. 1 liter |

The medium had a pH of 7.2, which was not adjusted. The inoculated medium was incubated for 72 hours as described above.

In a 40-liter fermentor a production medium of the following composition was prepared:

| Ingredient | Amount |
| --- | --- |
| Polysiloxane oil antifoam agent | 5 g. |
| Glycerol | 375 g. |
| Dextrose | 625 g. |
| Casein pancreatic hydrolysate peptone | 125 g. |
| Beef extract | 125 g. |
| NaCl | 125 g. |
| CaCO$_3$ | 50 g. |
| Deionized water | q.s. 24 liters |

The initial pH of the medium was 7.0. The medium was then sterilized by autoclaving at 120° C. for 30 minutes at 15–20 pounds per square inch pressure. After sterilization, the pH of the medium was 7.6.

Purified monensin (25 g.) dissolved in ethanol (200 ml.) was added to the sterilized medium, and the second-stage vegetative inoculum (700 ml.) prepared as described above was introduced.

The fermentation medium was aerated with sterile air at a rate of air per volume of medium per minute (v./v./m.) and was stirred with conventional agitators at 420 r.p.m. The inoculated medium was incubated at 30° C. for about 114 hours.

The course of the fermentation was followed by thin-layer chromatography on silica gel as described hereinabove. Early in the fermentation only monensin was present. Gradually a second spot indicated the presence of metabolite A-27106 sodium salt; and finally, only the spot for metabolite A-27106 sodium salt was present.

EXAMPLE 19

Isolation and Purification of A-27106 Sodium Salt

The fermentation broth, prepared as described in Example 18, was filtered, using a filter aid. The mycelial cake was extracted with methanol (about 5 l.) at room temperature. The methanol extract was filtered; the filtrate was concentrated under vacuum, removing the methanol and leaving an aqueous concentrate.

This aqueous concentrate was combined with the original broth filtrate. The combined solution (about 22 l.) was extracted twice with half-volumes of chloroform. The chloroform extracts were combined and concentrated under vacuum to about 400 ml. of a dark amber oil.

This oil, dissolved in chloroform, was decolorized over a 10-kg. carbon (Pittsburg "12 × 40") column, eluting with chloroform (about 5 l.). The chloroform eluate was evaporated under vacuum to give about 500 ml. of a colorless to pale-yellow oil.

The decolorized oil, in a minimal amount of chloroform, was then chromatographed over a 25-kg. column of silica gel (Grace, grade 62) in ethyl acetate. Elution was monitored by thin-layer chromatography as described earlier. After impurities were removed with ethyl acetate, the product was eluted from the column with ethyl acetate-methanol (19:1). The fractions containing the product were combined and evaporated to dryness under vacuum to give an amorphous, almost white product. The product was washed with hexane and dried to give about 12.84 g. of metabolite A-27106 sodium salt (one-spot material by tlc).

EXAMPLE 20

Production of A-27106 S. cinnamonensis and S. candidus.

Another method of producing metabolite A-27106 in fermentor culture is illustrated by the following procedure:

Streptomyces cinnamonesis ATCC 15413 was conventionally grown (see U.S. Pat. No. 3,501,568) in 55 ml. of medium in a 250-ml. shake flask, incubating for 47 hours to obtain a vegetative inoculum. This vegetative inoculum was added to 220 ml. of medium in a one-liter shake flask and was incubated for 21 hours to supply inoculum for seeding the fermentor.

The inoculum thus prepared was used to seed a 40-l. fermentor containing a heat-sterilized medium of the following composition:

| Ingredient | Amount |
| --- | --- |
| Glucose | 750.0 g. |
| Soybean meal | 625.0 g. |
| Soybean oil | 500.0 g. |
| Methyl oleate | 500.0 g. |
| Polysiloxane oil antifoam | 5.0 g. |
| Potassium chloride | 2.5 g. |
| Dipotassium hydrogen phosphate | 2.5 g. |
| Manganous chloride tetrachloride | 15.0 g. |
| Hydrated ferric sulfate | 7.5 g. |
| Calcium carbonate | 25.0 g. |
| Deionized water | q.s. 24 liters |

The resulting medium had a pH of 5.5 which was adjusted to pH 8.0 by addition of 10 N potassium hydroxide (15 ml.). The inoculated medium was incubated at 32° C. for 234 hours.

After 42 hours, aeration was increased from 0.5 to 1.1 v./v./m., and agitation was increased from 500 to 700 r.p.m. Monensin production was essentially complete after 210 hours, as determined by thin-layer bioassay with Bacillus subtilis ATCC 6633 as the detection organism.

After 234 hours, the fermentor contents were pasteurized to inactivate S. cinnamonensis. The following nutrients were then added to the fermentor:

| Ingredient | Amount |
| --- | --- |
| Dextrose | 750 g. |
| Soybean meal | 625 g. |
| Manganous chloride tetrahydrate | 15 g. |
| Calcium carbonate | 12.5 g. |
| Ferric sulfate hexahydrate | 7.5 g. |

| Ingredient | Amount |
|---|---|
| Potassium chloride | 2.5 g. |
| Dipotassium hydrogen phosphate | 2.5 g. |
| Methyl oleate | 250 ml. |
| Soybean oil | 250 ml. |
| Deionized water | q.s. 24 liters |

The pH was adjusted to 8.0 with 215 ml. of 5 N NaOH, and the medium was sterilized. The medium was then inoculated with a rapidly growing vegetative culture of *Streptomyces candidus* NRRL 5449 and was incubated for 137 hours at 30° C. The fermentation was aerated with sterile air at a rate of 0.5 v./v./m. The fermentation medium was atirred with conventional agitators first at 120 r.p.m., increasing after 16 hours to 420 r.p.m. and after 40 hours to 500 r.p.m. Dextrose (400 g.) was added at each of hours 44, 66.5, 89, 97, 113, and 127. Calcium carbonate (175 g.) was added at each of hours 72 and 99.

Thin-layer chromatography, as described hereinabove, was used to monitor the fermentation. After 137 hours, production of metabolite A-27106 was essentially complete. Work-up and purification of A-27106 sodium salt followed the procedures described in Example 20.

The polyether ionophorous antibiotics described above are active against a number of viruses of economic importance because of the economic losses the viruses cause through the infections and diseases they cause in animals and poultry. The anti-viral activity of these antibiotics has been demonstrated by tests run in tissue culture, as well as by in vivo results from tests run in dogs and pigs.

The antibiotics are thus shown to be useful for the moderation of the effects of viral infections and diseases in dogs and swine. These antibiotics are also considered potentially useful for the moderation of the effects of viral infections and diseases in cattle and poultry.

The viruses against which the antibiotics are efficacious in vitro include both DNA and RNA viruses classified as herpesvirus, including infections bovine rhinotracheitis (IBR); and feline rhinotracheitis virus (FRV). The antibiotics are also active against another DNA virus of the classification adenovirus, namely infectious canine hepatitis (ICH), as well as the DNA virus parvovirus, identified as panleukopenia virus. The antibiotics are also active against a number of classifications of RNA virus, as follows: a coronavirus, identified as transmissible gastroenteritis (TGE); two paramyxoviruses, identified as Newcastle disease virus (NDV), and canine distemper virus (CDV); and an RNA unclassified virus identified as bovine virus diarrhea (BVD).

The in vitro antiviral activity of the polyether ionophorous antibiotics was determined according to the procedure set forth below.

TEST 1

The in vitro tissue culture screens were conducted in monolayer cultures of susceptible mammalian cells. These screens used porcine kidney cells designated as LLC-$RK_1$-(Hull), ATCC No. CCL 106, available from the American Type Culture Collection, Registry of Animal Cell Lines, 12301 Parklawn Drive, Rockville, Maryland 20852; feline kidney cells (CRFK) available from the Cell Culture Laboratory, Naval Biomedical Research Laboratory, Oakland, California 94625; and canine kidney cells [MDCK(NBL-2)], also available from The American Type Culture Collection, supra.

The cell cultures were grown in test tubes measuring 16 × 150 mm., using aseptic tissue culture procedures. The MDCK cells were grown in a media comprising Earle's balanced salt solution, 0.5 percent lactalbumin hydrolysate, and 10 percent fetal calf serum. The $pK_1$ cells were grown in medium 199 plus 10 percent fetal calf serum. The CRFK cells were grown in Eagle's medium plus 10 percent fetal calf serum. When the cells in the test tubes had become reasonably confluent, about 3–5 days, the media in the tubes were changed to medium 199 plus fetal calf serum, except where indicated otherwise in Table 1. Fresh medium was added to the tubes just before the test compounds were introduced into the tubes. Other media similar to medium 199 may also be used at this stage of this process to maintain the cells after the cells become confluent. For examples of such other media, see *Methods of Tissue Culture*, Chapter VI, pp. 62–80, edited by Parker, 3rd edition (1962), [Hoeber Medical Division, Harper & Row, Publishers, 49 East 33rd Street, New York].

The cells of each tube were pretreated with dilutions of the test compound 4 hours before addition of the viruses. The antibiotics were formulated in the following manner for use in this pretreatment.

Four milligrams of an antibiotic were weighed out and dissolved in 2 ml. of a mixture of ethanol and dimethyl-sulfoxide (DMSO). This dilution is equivalent to a concentration of 2000 micrograms (mcg.) per milliliter. A 20-lambda pipette was used to dispense 20-lambda of the solution of the antibiotic to filter paper test discs. One lambda is equal to 0.001 milliliter. Each disc, then, when placed in a test tube containing 2 ml. of the tissue culture media, provided the test level of 20 mcg./ml.

Lower concentrations of the test antibiotics were prepared using two-fold dilutions. Thus, 0.5 ml. of the 2000 mcg./ml. standard concentration was transferred to 0.5 ml. of DMSO to provide a test solution having a concentration level of 1000 mcg./ml. This solution was applied to the discs at the rate of 20 lambda per disc. Each such disc, placed in a test tube containing 2 ml. of the tissue culture media, provided a test level of 10 mcg./ml. In a similar manner, the other lower concentrations of the test compounds were prepared and applied to the filter paper test discs. Levels tested were 20, 10, 5, 2.5, 1.25, 0.62, 0.32, 0.25, 0.16, 0.08, 0.04, 0.02, 0.01, and 0.005 mcg./ml.

Four hours after the addition of the compound to be tested to the media in the tubes, the different viruses were added. The viruses were added in such an amount as to give a concentration of about 100 virus particles per 0.1 ml. of media. Each test tube contained a volume of 2 milliliters, comprising cells, media, and virus, with the concentration of the test compound being about 20 microgram per milliliter as a first test concentration. If this concentration ultimately was found to be too high, it was diluted and retested, until a suitable screen level was determined. The test tubes were placed in roller drums and agitated gently while being incubated at about 37° C. for from two to seven days. Three tubes were used for each virus at each concentration of antibiotic. Three tubes containing only cells, three tubes, containing virus, and tubes containing only test compound, plus two additional tubes containing the next higher dilution of virus were also run.

The tubes were examined under a microscope on a daily basis to determine the inhibition of cytopathic effects (CPE) in the cells. The CPE results observed 4–5 days after the addition of the viruses to the tubes are the results recorded in Table 1, which follows hereinafter.

The viruses screened in this test include: transmissible gastroenteritis (TGE); Newcastle disease virus (NDV); infectious canine hepatitis (ICH); infectious bovine rhinotracheitis (IBR); bovine virus diarrhea (BVD); and feline rhinotracheitis virus (FRV).

The results are set forth in Table 1 which follows. In the table, Column 1 identifies the test compound, and Columns 2–4, the concentration of test compound which inhibits the growth of the particular virus.

TABLE 1

IONOPHOROUS ANTIBIOTIC ACTIVITY IN TISSUE CULTURE

| Compound | TGE Active | NDV Active | ICH Active |
|---|---|---|---|
| A150 | 0.08 | — | — |
| A204 (complex) | 0.04 | — | — |
| A204II | 0.16 | — | 0.08 |
| A204III | 5.0 | — | — |
| A204I ethyl | 0.16 | — | — |
| A204I methyl | 0.32 | 0.05 | 0.32 |
| A204I n-propyl | 1.25 | 0.32 | — |
| X-206 | 0.02 | — | — |
| A28086A | 0.25 | 0.02 | — |
| A28086D | 0.02 | 0.02 | NT |
| A28695A | 0.08 | — | 0.32 |
| A28695B | 0.16 | 2.0 | — |
| Monensin | 0.02 | — | — |
| Monensin B | 0.25 | — | — |
| Carbomonensin | 2.5 | — | — |
| Dihydromonensin | — | 10.0 | — |
| Nigericin | 0.08 | 0.5 | — |
| Lasalocid (X-537A) | 0.005 | N | NT |
| Cell line | PK$_1$ | PK$_1$ | MDCK |
| % fetal calf serum | 2% | 1% | 1% |

| Compound | IBR Active | BVD Active | FRV Active |
|---|---|---|---|
| A150 | 0.02 | 0.005 | 0.01 |
| A204 (complex) | 0.005 | 0.005 | — |
| A204II | — | — | — |
| A204III | 0.32 | — | — |
| A204I ethyl | 0.32 | — | 0.32 |
| A204I methyl | — | — | 0.08 |
| A204I n-propyl | 0.02 | — | 0.16 |
| X-206 | 0.02 | — | — |
| A28086A | 0.02 | NT | — |
| A28086D | — | NT | NT |
| A28695A | 0.02 | NT | — |
| A28695B | — | NT | — |
| Monensin | — | NT | — |
| Monensin B | 0.08 | NT | — |
| Carbomonensin | 0.32 | NT | — |
| Dihydromonensin | 5.0 | NT | — |
| Nigericin | 0.005 | NT | — |
| Lasalocid (X-537A) | N | NT | NT |
| Cell line | CRFK | PK$_1$ | CRFK |
| % fetal calf serum | 2% | 0% | 0% |

Initial levels run were 20.0, 5.0, 1.25, 0.32, 0.08 and 0.2 μg./ml. (all activity reported in μg./ml.)

NT - Not tested
— - Not active or no toxic level reached
N - Inactive
TGE - Transmissible gastroenteritis
NDV - Newcastle disease virus
ICH - Infectious canine hepatitis
IBR - Infectious bovine rhinotracheitis
BVD - Bovine virus diarrhea TABLE 1-continued

IONOPHOROUS ANTIBIOTIC ACTIVITY IN TISSUE CULTURE

FRV - Feline rhinotracheitis virus

TEST 2

The evaluation of the efficacy of the antibiotic monensin against infectious canine hepatitis (ICH) in susceptible dogs was carried out in the following manner:

Four dogs, litter mates of approximately equal weights, were used in the test. The monensin was formulated by adding it to a small amount of ethyl alcohol and shaking for a period of time until solution was complete, then adding polyethyleneglycol 200 (PEG 200). The concentration was 5 mg./ml. The monensin, formulated as described, was administered subcutaneously at 8 a.m. and 3 p.m. on day 1 of the test to two of the dogs at a dosage of 0.5 mg. of active ingredient per kilogram of body weight. This dosage was repeated twice daily for the nine days of the test. Two of the dogs received no treatment and served as controls.

On day 2 of the test, all the dogs were challenged with 1.0 ml. of a 1:12 dilution of the Mirandola strain of ICH given intravenously. The Mirandalo strain of ICH is available from the Animal and Plant Health Inspection Service, Enforcement Operations, Veterinary Biology Division, P.O. Box 844, Ames, Iowa 50010.

The two dogs which did not receive the test compound died by the fourth day of the test, and at necropsy showed typical lesions of ICH.

One of the treated dogs died seven days post-challenge, while the other dog survived. The dog which survived to the end of the 9-day test was sacrificed and at necropsy showed no lesions of ICH.

TESST 3

The efficacy of some of the polyether ionophorous antibiotics in controlling transmissible gastroenteritis (TGE) in swine was determined in the following manner:

A balanced swine farrowing ration having the following composition was used:

| INGREDIENT | PERCENT | LBS./TON |
|---|---|---|
| Corn, Yellow, Ground | 65.10 | 1302 |
| Soybean Oil Meal, Solvent Extracted, Dehulled, 50% | 18.50 | 370 |
| Dried Beet Pulp | 10.00 | 200 |
| Dicalcium Phosphate | 2.90 | 58 |
| Calcium Carbonate | 1.20 | 24 |
| Swine Vitamin Premix, SW-03[1] | 1.10 | 22 |
| Salt (NaCl) | 0.55 | 11 |
| Choline Chloride, 25% | 0.35 | 7 |
| Trace Mineral Premix, AN-03[2] | 0.15 | 3 |
| Vitamin A Premix[3] | 0.10 | 2 |
| Methionine Hydroxy Analogue, 93% | 0.05 | 1 |
| Total | 100.00 | 2000 |

[1]Each kg. of premix contains the following: 77,161 USP units Vitamin D$_2$; 2,205 Int. units Vitamin E; 441 mg. riboflavin; 1,620 mg. pantothenic acid; 2,205 mg. niacin; 4.4 mg. Vitamin B$_{12}$; 441 mg. Vitamin K; 19,180 mg. choline; 110 mg. folic acid; 165 mg. pyridoxine; 110 mg. thiamine; 22 mg. biotin.
[2]Each kg. of premix contains the following: 50 gm. of manganese as manganese sulfate; 100 gm. of zinc as zinc carbonate; 50 g. of iron as ferrous sulfate; 5 gm. of copper as copper oxide; 1.5 gm. of iodine as potassium iodide and 150 gm. maximum and 130 gm. minimum calcium as calcium carbonate.
[3]Each kg. of premix contains 6,613,800 USP units Vitamin A.

To this ration was added a premix comprising solvent-extracted soybean feed and the test antibiotic. One pound of premix was prepared for each 200 pounds of feed,. Thus, to prepare the premix for 200 lb. of feed, ten grams of antibiotic was added to a small amount of solvent-extracted soybean feed and ground in a mortar and pestle. The mixture was then diluted to one pound with additional solvent-extracted soybean feed and mixed in a small Hobart mixer. This premix was then added to the 200 lb. of the ration described above and mixed according to standard techniques, providing a level of 100 g./ton of antibiotic in the basal ration. Larger or smaller quantities of medicated ration with varying levels of antibiotic were prepared by appropriately varying the quantity of antibiotic in the premix and the quantity of basal ration used.

Using medicated feed prepared as described above, sows were fed at rates of from 2.5 to 10.0 grams of an antibiotic per 100 pounds of feed for from 1 day, to preferably 7 to 10 days, prior to farrowing, and continuing thereafter to the end of the test. The medicated feed was available ad libitum, to consumption level, together with water, to the sows. Usually each sow consumed about 6-8 lb. of food per day. For administration to the piglets, the test antibiotic was dissolved in a small quantity of ethanol, and the solution suspended in polyethylene glycol 200 (PEG 200). Other suitable suspending agents include corn oil, or refined soybean oil. The young pigs, 2 to 4 days old, were administered the suspension of the antibiotic by gavage at the rate of 0.5 mg. to 50 mg. per pound, three times a day. young piglets normally range in weight from 1.5 to 5.0 pounds. The dose of the antibiotic was adjusted so as to be about 0.5 to 2 ml. in volume. Treatment continued for 5-10 days.

Twenty-four hours after treatment began, the piglets were challenged by administration by gavage to each pig of 1 ml. of a $10^{-4}$ dilution in sterile saline of Purdue or Miller strain of TGE. Purdue purdue strain of TGE virus is available from Dr. E. O. Haelterman, School of Veterinary Medicine, Purdue University, West Lafayette, Indiana 47907. The Miller strain of TGE virus is available from Dr. E. H. Bohl, Ohio Agricultural Research and Development Center, Wooster, Ohio 44691. One or two pigs were used as virus controls and were removed from the sow at the time of challenge.

Evaluation of the efficacy of the antiviral activity of the antibiotic was accomplished by observing weight gain, diarrhea, vomiting, mortality of the piglets, the sow temperature, and sow scouring.

The results of the test are recorded in Table 2, which follows. In the table, Column 1 identifies the test antibiotic; and Column 2 shows the number of pigs which survived in comparison to the number of pigs in the test.

TABLE 2

| Antibiotics | TGE STUDIES Survivors/No. in Test |
|---|---|
| Monensin | 8/25 |
| A-28086 | 3/6 |
| A28695A | 2/4 |
| A28695B | 3/5 |
| Nigericin | 4/7 |
| Carbomonensin | 2/5 |
| Control | 0/5 |

The polyether ionophorous antibiotics usable in the novel method of this invention are effective in the moderation of the effects of viral infection in baby pigs, at dosages of from about 0.1 mg. to about about 100 mg./kg. of body weight when given to the baby pigs by gavage. These antibiotics are effective in moderating the effects of viral infections in sows through oral administration of the antibiotics in the feed at rates of from about 2.5 to about 10 gm./100 lb. of feed.

These antibiotics are effective in moderating the effects of ICH in dogs when administered subcutaneously at the rate of from about 0.1 mg. to about 10 mg./kg. of body weight per day for about 7 to about 14 days.

These antibiotics are also considered potentially useful for the moderation of infectious diseases of cattle and poultry caused by the viruses described herein.

It has been found that the polyether ionophorous antibiotics described above as being useful in the present novel method are easily administered to animals by mixing the antibiotic in the animal feed. Parenteral administration is also a suitable method for administration of the antibiotics. The antibiotics can also be administered by insufflation by blowing the antibiotic, in the form of a medicated dust, into an enclosed space or room wherein the animals or poultry are held. The animals or poultry thus breathe the medicated dust present in the air, and the medicated dust also is taken into the body by contact with the eyes, which process is termed intraocular injection.

The most practical way to treat animals with the antibiotic compounds useful in this method is by the formulation of the compound into the feed supply. Any type of feed may be medicated with the antibiotic compounds, including common dry feeds, liquid feeds, and pelleted feeds.

The methods of formulating drugs into animal feeds are well-known. It is usual to make a concentrated drug premix as a raw material for medicated feeds. For example, typical drug premixes may contain from 1 to bout 200 g. of drug per pound of premix. The wide range results from the wide range of concentration of drug which may be desired in the final feed. Premixes may be either liquid or solid.

The formulation of feeds for animals or poultry, which feeds contain the proper amounts of the antibiotic compounds for useful treatment, is mainly a matter of arithmetic. It is necessary only to calculate the amount of compound which it is desired to administer to each animal, to take into account the amount of feed per day which the animal eats and the concentration of antibiotic compound in the premix to be used, and then calculate the proper concentration of antibiotic compound in the feed.

All of the methods of formulating, mixing, and pelleting feeds which are normally used in the animal feed art are entirely appropriate for manufacturing feeds containing the antibiotic compounds useful in this novel method.

The methods of formulating these polyether ionophorous antibiotics for parenteral administration are well-known in the veterinary pharmaceutical art. Effective injectable compositions containing the antibiotics may be in either suspension or solution form. Solutions comprise the active antibiotic dissolved in a physiologically-acceptable carrier comprising a solvent together with the necessary preservatives, such as benzyl alcohol, and buffers. Useful solvents may be, depending on the antibiotic chosen, alcohols, glycols, or inert oils such as vegetable oils or highly refined mineral oils.

Injectable suspension compositions employ a nonsolvent for the antibiotic, with adjuvants, as a carrier. The nonsolvent can be for example, depending on the antibiotic chosen, a vegetable oil such as peanut oil, corn oil, or sesame oil, or a glycol, such as one of the polyethylene glycols, or water.

Suitable physiologically acceptable adjuvants are necessary to keep the active compounds suspended in suspension compositions. The adjuvants may be chosen from among the thickeners, such as carboxymethylcellulose, polyvinylpyrrolidone, gelatin, and the alginates. Many classes of surfactants also serve to suspend the antibiotics. For example, lecithin, alkylphenol polyethylene oxide adducts, naphthalenesulfonates, alkylbenzenesulfonates, and the polyoxyethylene sorbitan esters are useful for suspending the antibiotics in liquid nonsolvents.

Many substances which affect the hydrophilicity, density, and surface tension of the liquid nonsolvent can assist in making injectable suspensions in individual cases. For example, silicone anti-foams, glycols, sorbitol, and sugars can be useful suspending agents.

The polyether ionophorous antibiotics are formulated as dusts or powders when it is desired to administer the antibiotics by insufflation. Typically, the antibiotics are mixed with talc, diatomaceous earth, or some other inert substance as an adjuvant, to form a medicated powder or dust It is not intended that the scope of this invention be limited to any particular formulations or methods of administration. The invention is a method of moderating the effects of viral diseases in dogs and swine by the oral or parenteral administration of certain antibiotics. However the administration may be accomplished, it is regarded as being within the scope of the novel method of moderating the effects of viral infections in dogs and swine.

We claim:

1. A method for moderating the effects of a viral infection selected from the group consisting of transmissible gastroenteritis in swine and infectious canine hepatitis in dogs which comprises administering to the animal host an effective amount of a polyether ionophorous antibiotic selected from the group consisting of monensin, A-28086, A28695, and carbomonensin.

2. A method of claim 1 wherein the animal host is swine, the viral infection is transmissible gastroenteritis, and the polyether ionophorous antibiotic is selected from the group consisting of monensin, A-28086, A28695 and carbomonensin.

3. The method of claim 2 wherein the polyether ionophorous antibiotic is A28086.

4. The method of claim 2 wherein the polyether ionophorous antibiotic is A28695.

5. The method of claim 2 wherein the polyether ionophorous antibiotic is monensin.

6. The method of claim 1 wherein the animal host is dogs, the viral infection is infectious canine hepatitis, and the polyether ionophorous antibiotic is monensin.

* * * * *

UNITED STATES PATENT AND TRADEMARK OFFICE
CERTIFICATE OF CORRECTION

PATENT NO. : 3,995,027
DATED : November 30, 1976
INVENTOR(S) : Gale et al.

It is certified that error appears in the above-identified patent and that said Letters Patent are hereby corrected as shown below:

On the title page the list of inventors should read as follows:

Charles Gale, Indianapolis
    Larry R. McDougald, Greenfield
    Janet D. Nelson, Indianapolis,
        all of Ind.

Column 1, line 35, after "et al.," insert --[Academic Press, New York and London (1973)]--.

Column 1, line 41, "inophorous" should read ---ionophorous---.

Column 1, line 46, "inophorous" should read ---ionophorous---.

Column 2, line 2, after "Microbial Products" insert --[ edited by Laskin et al., published by CRC Press, Inc., Cleveland, Ohio (1973)]--.

Column 2, line 29, "monensis" should read ---monensin---.

Column 3, line 2, "3,832,619" should read ---3,932,619---.

Column 4, line 17, "A2086" should read ---A28086---.

Column 4, line 62, "1.5404" should read ---1.5405---.

Column 5, line 67, "tilted" should read ---titled---.

UNITED STATES PATENT OFFICE
CERTIFICATE OF CORRECTION

Patent No. 3,995,027    Dated November 30, 1976

Inventor(s) Charles Gale et al

It is certified that error appears in the above-identified patent and that said Letters Patent are hereby corrected as shown below:

Column 6, line 22, the empirical formula should read ---$C_{44}H_{74}O_{11}$.---

Column 9, line 3, "te" should read ---the---.

Column 9, line 39, "RECOVERS" should read ---RECOVERY---.

Column 16, line 68, "Norther" should read ---Northern---.

Column 19, line 52, "1147" should read ---11.47---.

Column 22, line 24, "cinnamonesis" should read ---cinnamonensis---.

Column 23, line 17, "atirred" should read ---stirred---.

UNITED STATES PATENT OFFICE
CERTIFICATE OF CORRECTION

Patent No. 3,995,027　　　　　　　　　　　Dated　November 30, 1976

Inventor(s)　Charles Gale et al.

It is certified that error appears in the above-identified patent and that said Letters Patent are hereby corrected as shown below:

Column 26, line 37, "TESST" should read ---TEST---.

Column 27, line 28, "young" should read ---Young---.

Column 27, line 36, "Purdue purdue strain" should read ---The Purdue strain---.

Column 28, line 36, "bout" should read ---about---.

Signed and Sealed this

Seventeenth Day of May 1977

[SEAL]

Attest:

RUTH C. MASON
*Attesting Officer*

C. MARSHALL DANN
*Commissioner of Patents and Trademarks*